US008795285B2

(12) United States Patent  (10) Patent No.: US 8,795,285 B2
Kwon  (45) Date of Patent: Aug. 5, 2014

(54) SPINAL FACET FUSION DEVICE AND METHOD OF OPERATION

(76) Inventor: Brian Kwon, Boston, MA (US)

( * ) Notice: Subject to any disclaimer, the term of this patent is extended or adjusted under 35 U.S.C. 154(b) by 213 days.

(21) Appl. No.: 13/276,996

(22) Filed: Oct. 19, 2011

(65) Prior Publication Data

US 2013/0103152 A1 Apr. 25, 2013

(51) Int. Cl.
*A61B 17/58* (2006.01)
*A61B 17/60* (2006.01)
*A61F 2/00* (2006.01)

(52) U.S. Cl.
USPC ............................................. 606/96; 606/99

(58) Field of Classification Search
USPC ............. 606/86 R, 246–249, 96, 99; 600/205
See application file for complete search history.

(56) References Cited

U.S. PATENT DOCUMENTS

| | | | |
|---|---|---|---|
| 6,635,062 B2 * | 10/2003 | Ray et al. ..................... | 606/96 |
| 7,223,269 B2 | 5/2007 | Chappuis | |
| 7,517,358 B2 | 4/2009 | Petersen | |
| 7,708,761 B2 | 5/2010 | Petersen | |
| 7,837,713 B2 | 11/2010 | Petersen | |
| D629,106 S | 12/2010 | Horton et al. | |
| D629,905 S | 12/2010 | Horton et al. | |
| 7,901,439 B2 | 3/2011 | Horton | |
| 7,998,172 B2 | 8/2011 | Blain | |
| 8,021,392 B2 | 9/2011 | Petersen | |
| 8,070,782 B2 | 12/2011 | McKay | |
| 8,080,046 B2 | 12/2011 | Suddaby | |
| 8,133,261 B2 | 3/2012 | Fisher et al. | |
| 8,162,981 B2 | 4/2012 | Vestgaarden | |
| 8,187,304 B2 | 5/2012 | Malek | |
| 8,197,513 B2 | 6/2012 | Fisher et al. | |
| 8,231,661 B2 | 7/2012 | Carls et al. | |
| 8,267,966 B2 | 9/2012 | McCormack et al. | |
| 8,348,979 B2 | 1/2013 | McCormack | |
| 8,361,152 B2 | 1/2013 | McCormack et al. | |
| 8,425,530 B2 | 4/2013 | Winslow et al. | |
| 2007/0270896 A1 | 11/2007 | Perez-Cruet | |
| 2008/0108991 A1 | 5/2008 | von Jako | |
| 2008/0140132 A1 | 6/2008 | Perez-Cruet | |
| 2009/0076555 A1 * | 3/2009 | Lowry et al. .................. | 606/280 |
| 2009/0149862 A1 | 6/2009 | Kim | |

* cited by examiner

*Primary Examiner* — Andrew Yang
*Assistant Examiner* — Diana S Jones
(74) *Attorney, Agent, or Firm* — Cantor Colburn LLP

(57) ABSTRACT

A spinal facet fusion device is provided. The device includes a working sleeve having a first surface with a first port and a second port extending there through. The first port has a first perimeter and the second port having a second perimeter, wherein the first port is larger than the second port. A guide wire sleeve having a body with a proximal end and a distal end and a first outer perimeter is provided. The first outer perimeter is sized and shaped to be slidingly disposed within the second port, the guide wire sleeve having a channel extending longitudinally from the proximal end through the distal end, the body further having a stop feature on the distal end. An implementing device having a second outer perimeter is sized to be slidingly received within the first perimeter.

19 Claims, 8 Drawing Sheets

SPINAL FACET FUSION DEVICE AND METHOD OF OPERATION

BACKGROUND OF THE INVENTION

The subject matter disclosed herein relates to a spinal facet fusion device and in particular to a percutaneous wire guide assisted spinal facet fusion device.

Existing techniques for spinal facet fusion involve placing a block of material, most commonly bone, into a prepared facet joint. Facet joint fusion provides the biological process necessary to achieve a fusion at the joint. Placing posterior instrumentation alone will often not result in fusion and can cause a clinical issue that results in pain or additional surgery. Therefore, the combination of facet joint fusion and posterior instrumentation, such as pedicle screws for example, provides the necessary combination that maximizes likelihood of achieving solid bony fusion.

Minimally invasive (MI) spinal fusion has gained increasing popularity. MI fusion techniques provide advantages in reducing muscle disruption, blood loss and pain. The commonest technique of MI spinal fusion is placement of pedicle screws through small percutaneous skin incisions. Placement of the pedicle screw may block access to the facet joint and eliminate the opportunity to achieve biological fusion. Therefore, it is desirable to perform facet fusion prior to placement of the pedicle screws.

Difficulties may occur when performing MI spinal fusion using percutaneous pedicle screws due to the introduction of a separate device in or around the screw in order to gain facet fusion. This disrupts the work flow of the surgery and may lead to an increase in soft tissue trauma. Further, placement of pedicle screws alone, without posterior fusion may be a non-reimbursable procedure that may result in increased medical cost for the patient.

Accordingly, while existing MI spinal fusion techniques are suitable for their intended purpose the need for improvement remains, particularly in providing a device for spinal fusion through the same incision used for screw placement.

BRIEF DESCRIPTION OF THE INVENTION

According to one aspect of the invention, a spinal facet fusion device is provided. The spinal facet fusion device includes a working sleeve having a first surface with a first port and a second port extending therethrough. The first port has a first perimeter and the second port having a second perimeter, wherein the first port is larger than the second port. A guide wire sleeve is provided having a body with a proximal end and a distal end and a first outer perimeter. The first outer perimeter is sized and shaped to be slidingly disposed within the second port. The guide wire sleeve has a channel extending longitudinally from the proximal end through the distal end, the body further having a stop feature on the distal end. An implementing device has a second outer perimeter sized to be slidingly received within the first perimeter.

According to another aspect of the invention, a spinal facet fusion device is provided. The spinal facet fusion device includes a working sleeve having a first surface and a second surface, the working sleeve having a first port and a second port extending through the first surface and the second surface, the first port having a first perimeter and the second port having a second perimeter. The first port is sized larger than the second port, the second surface having features for engaging a patient's bone. A guide wire sleeve is provided having a first body with a proximal end and a distal end and a first outer perimeter. The first outer perimeter is sized and shaped to be slidingly disposed within the second port, the guide wire sleeve having a channel extending longitudinally from the proximal end through the distal end, the first body further having a first stop feature on the distal end. The second surface is arranged to be removably in contact with the first stop feature. An implementing device is provided having a second outer perimeter sized to be slidingly received within the first perimeter.

According to yet another aspect of the invention, a method is provided that includes providing a working sleeve having a first surface with a first port and a second port extending therethrough. The first port has a first perimeter and the second port has a second perimeter, wherein the first port is larger than the second port. A guide wire sleeve is provided having a body with a proximal end and a distal end and a first outer perimeter, the first outer perimeter being sized and shaped to be slidingly disposed within the second port. The guide wire sleeve has a channel extending longitudinally from the proximal end through the distal end, the body further having a stop feature on the distal end. An implementing device is provided having a second outer perimeter sized to be slidingly received within the first perimeter. The guide wire sleeve is slid into the second port. The implementing device is slid into the first port.

These and other advantages and features will become more apparent from the following description taken in conjunction with the drawings.

BRIEF DESCRIPTION OF THE DRAWING

The subject matter, which is regarded as the invention, is particularly pointed out and distinctly claimed in the claims at the conclusion of the specification. The foregoing and other features, and advantages of the invention are apparent from the following detailed description taken in conjunction with the accompanying drawings in which:

The detailed description explains embodiments of the invention, together with advantages and features, by way of example with reference to the drawings.

DETAILED DESCRIPTION OF THE INVENTION

Referring to FIGS. 1-7, a spinal facet fusion device is provided. The spinal facet fusion device provides advantages in allowing spinal facet fusion utilizing a guide-wire that is already in place prior to placement of the pedicle screws. The spinal facet fusion device assists surgeons in directing them to the facet joint, in exposing the facet joint and preparing the facet join for fusion through the same incision as is used for screw placement.

Figure 1A:
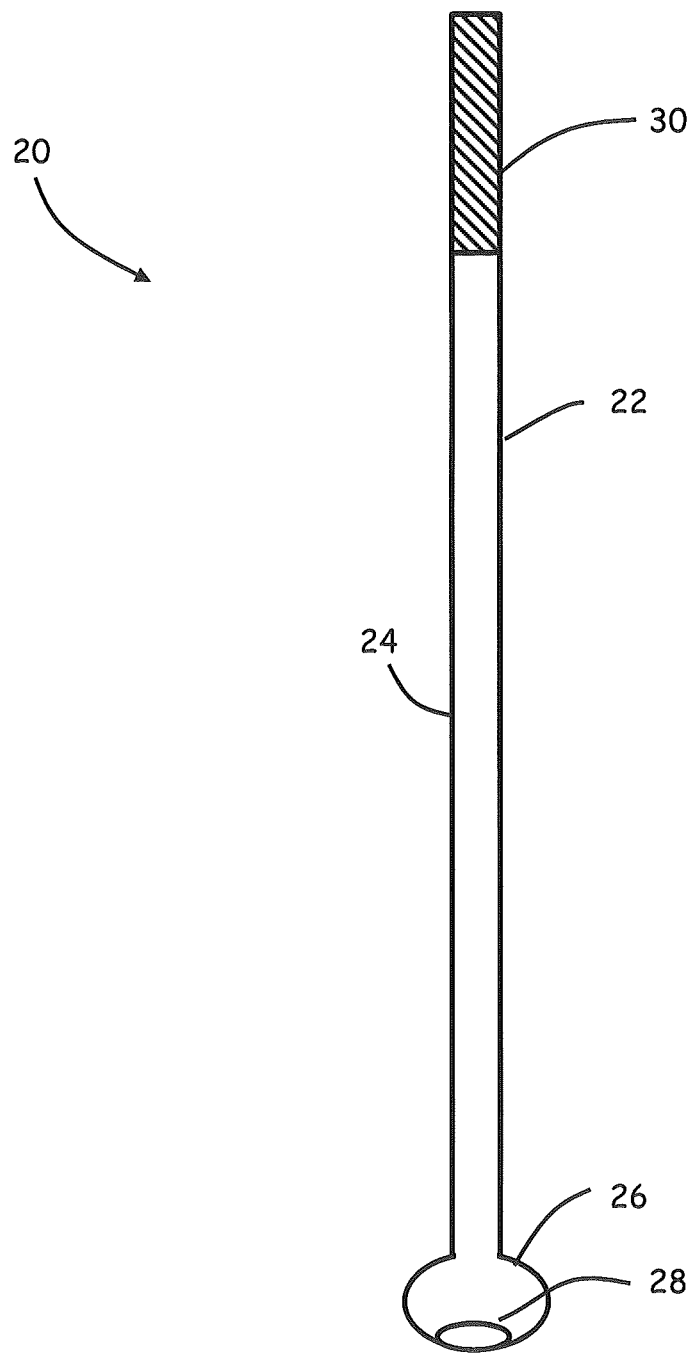
FIG. 1A is a side view of a guide-wire sleeve in accordance with an embodiment of the invention.
Figure 1B:
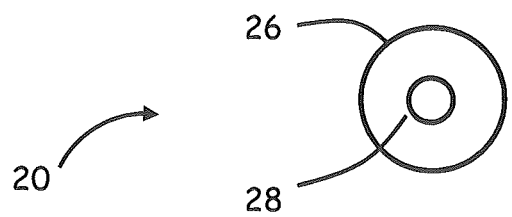
FIG. 1B is an end view of the guide-wire sleeve of FIG. 1A.

The spinal facet fusion device includes a guide-wire sleeve 20 shown in FIGS. 1A and 1B. The guide-wire is first placed into the pedicle using well-known radiographic assisted techniques. The guide-wire sleeve 20 provides a positive stop so that the fusion preparation steps do not violate the spinal canal. The guide-wire sleeve 20 includes an outer sheath 22 having a cylindrical portion 24 and a rounded or spherical portion 26. A channel 28 extends through the guide-wire sleeve 20. The channel 28 is sized to receive the guide wire (not shown). The rounded portion 26 is a feature that reduces the risk of violating the spinal canal while allowing consistent measured amount of countersink of graft material into the facet joint. A marking indicia 30 is provided on a proximal end of the guide-wire sleeve 20 to provide an indication to the surgeon of the relative position of the implementing devices discussed below. In one embodiment, the indicia 30 is used to provide feedback to the surgeon that the sleeve 20 is at risk spinal canal violation. In the exemplary embodiment, the guide-wire sleeve 20 may be made from a suitable bio-compatible material such as but not limited to titanium, stainless steel, or radiolucent plastic such as PEEK.

Figure 2A:
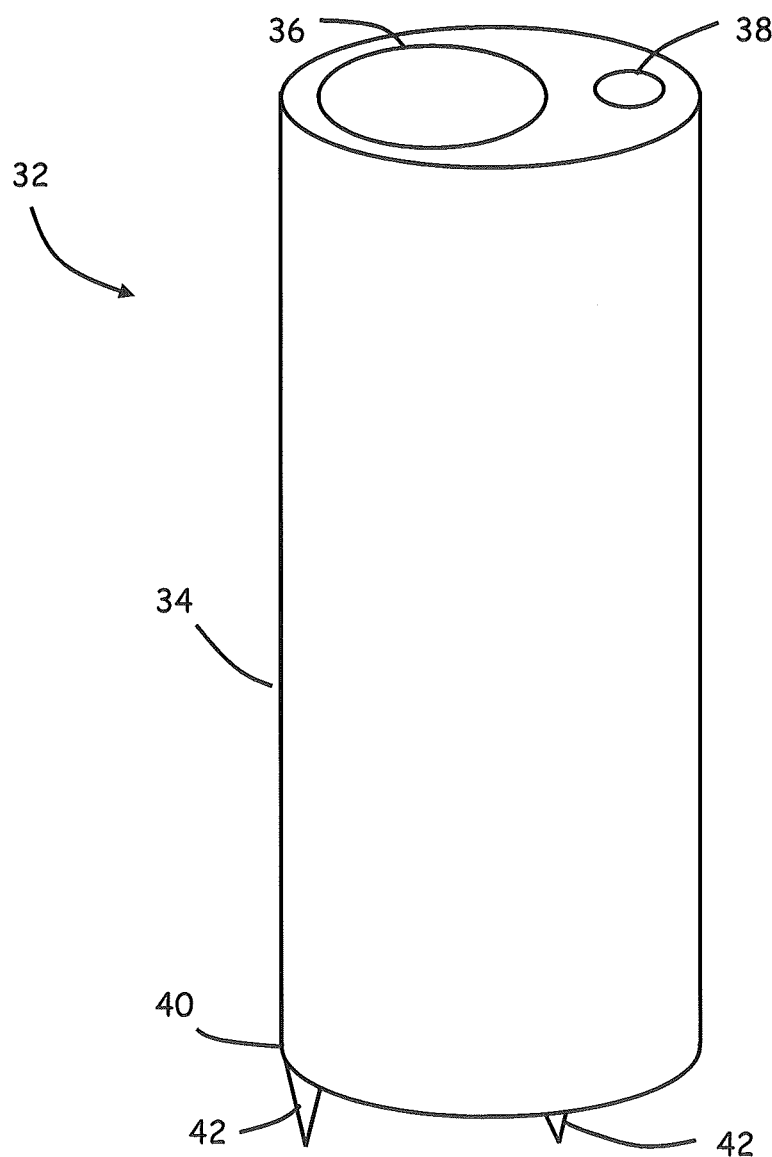
FIG. 2A is an perspective view of a working sleeve in accordance with an embodiment of the invention.
Figure 2B:
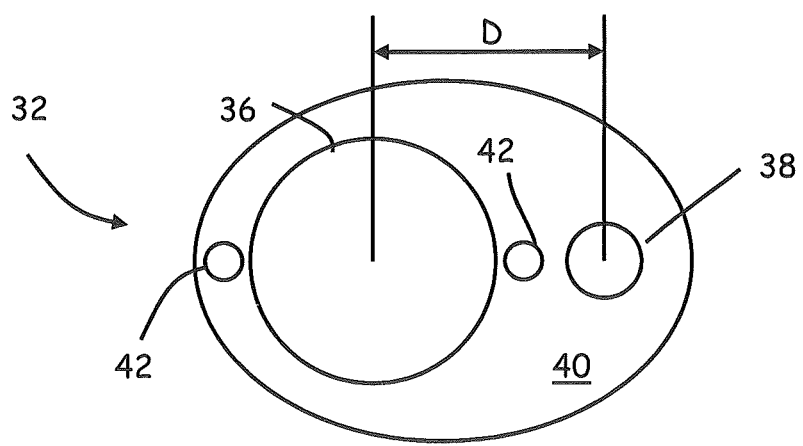
FIG. 2B is an end view of the working sleeve of FIG. 2A

Referring now to FIGS. 2A-2B, a working sleeve 32 is shown that supports and guides the facet fusion preparation devices during the surgery. The working sleeve 32 includes a body portion 34 having a pair of bores or ports 36, 38 extending longitudinally therethrough. The first port 38 is sized to receive the cylindrical portion 24 of the guide-wire sleeve 20. The second or working port 36 is sized to receive one or more implementing devices discussed below that allow the preparation and placement of the graft in the facet joint at a desired predetermined distance D from the guide wire. In one embodiment, the port 36 is sized to receive an implementing device having a 15-18 millimeter diameter. In the exemplary embodiment, a distal end 40, is provided that includes features such as teeth 42 that are sized to engage the patients bone to prevent rotation of the working sleeve 32 during use. In another embodiment, the end 40 may be contoured with a sharp edge to engage the patients bone. In the exemplary embodiment, the working sleeve 32 is made from a suitable bio-compatible material such as but not limited to titanium, stainless steel or radiolucent plastic such as PEEK.

It should be appreciated that multiple working sleeves may be provided that allow for the desired distance D to match patient anatomy. It should be appreciated that the working sleeve 32 provides advantages in allowing implementing devices that prepare and cut a round shape that allows for the insertion of a round-shaped graft into the facet joint.

Figure 3:
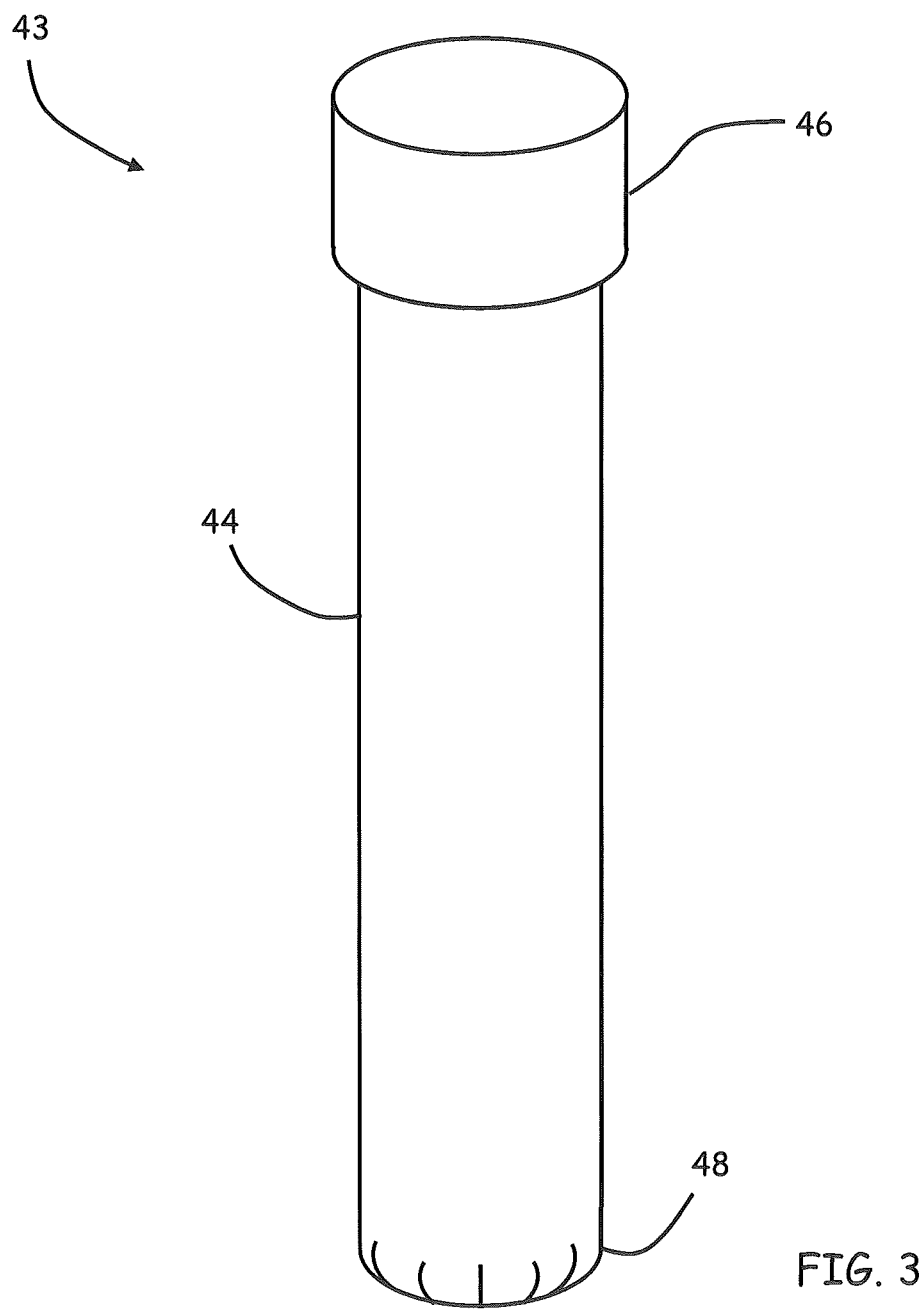
FIG. 3 is a perspective view of a soft tissue dissector for use with the working sleeve of FIG. 2.

A soft tissue dissector 43 is shown in FIG. 3 for clearing soft tissue from the area over the top of the facet joint. The dissector 43 has a generally cylindrical body 44 having an outer perimeter sized to be received within working port 36. The body 44 includes an attachment feature 46 that provides a stop when inserted into the working port 36 to ensure the desired length of the dissector 43. On a distal end 48, the dissector 43 includes a round to bullet-shaped end 48 that allows for atraumatic soft-tissue dissection. In the exemplary embodiment, the dissector 43 is made from a bio-compatible material such as but not limited to titanium, stainless steel, or radiolucent plastic such as PEEK. In one embodiment, the body 44 has a diameter of 15-18 millimeters and a length of about 30 millimeters.

Figure 4:
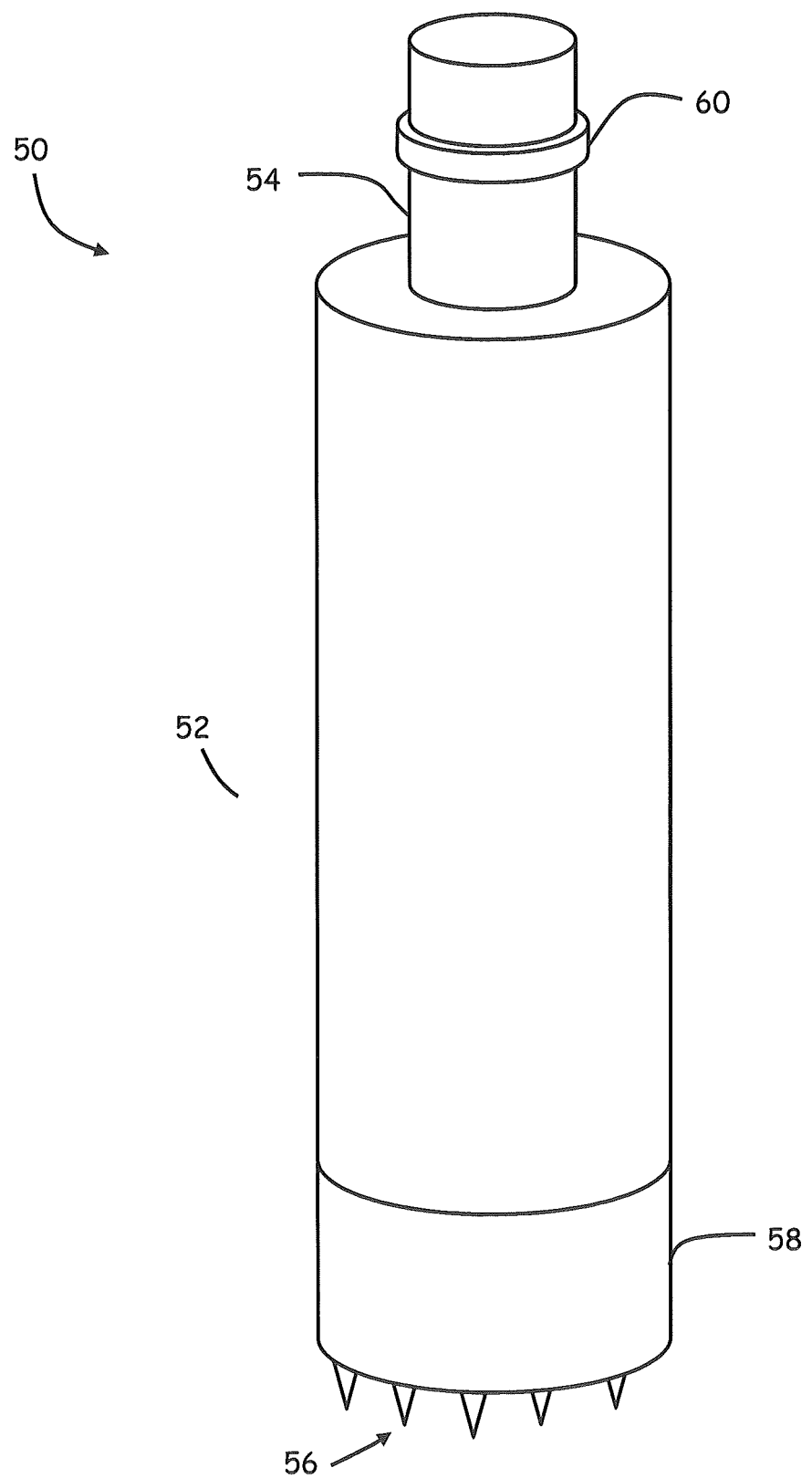
FIG. 4 is a perspective view of a soft tissue rasp for use with the working sleeve of FIG. 2.
Figure 5:
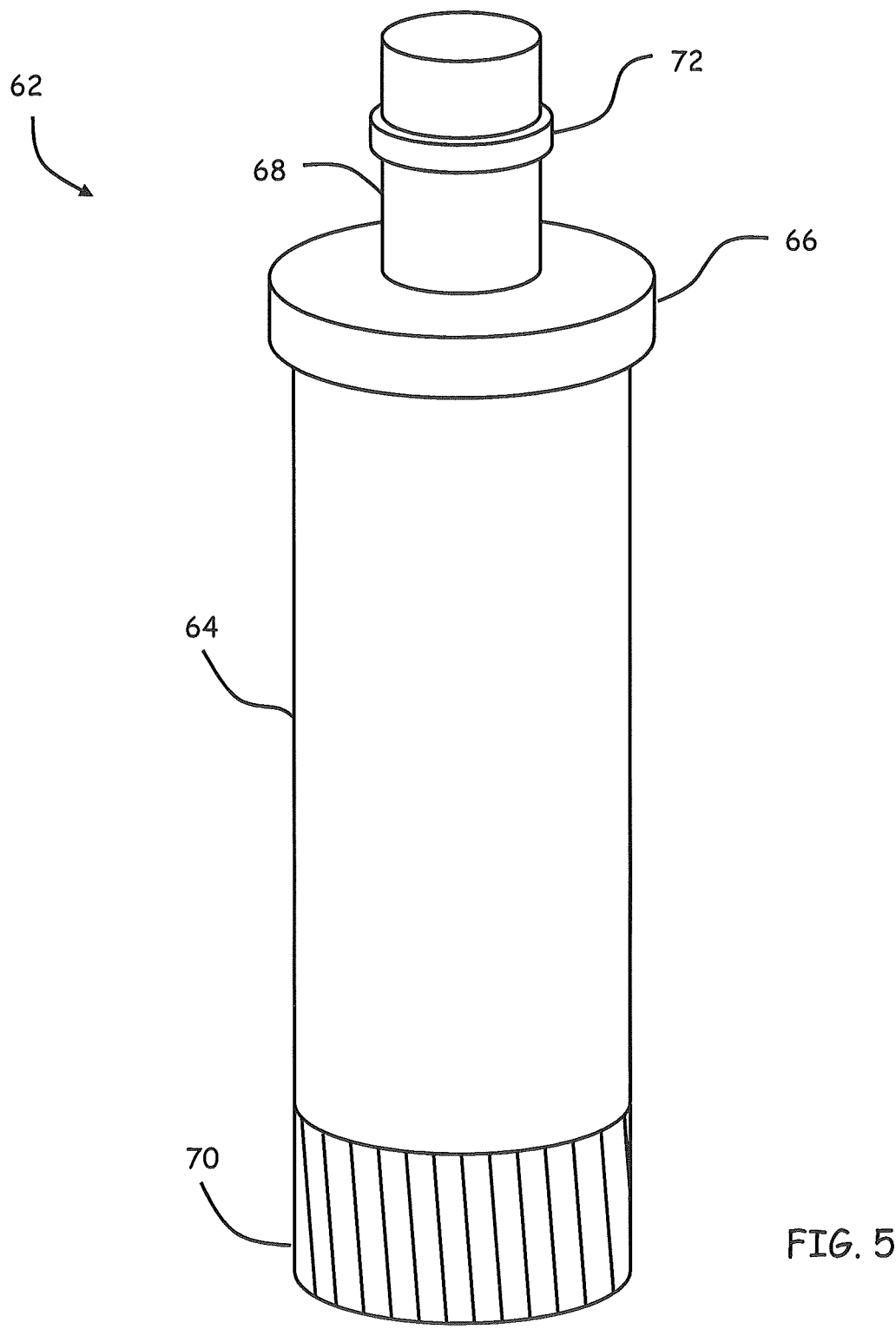
FIG. 5 is a perspective view of a drill device for use with the working sleeve of FIG. 2.

A soft tissue rasp 50 shown in FIG. 4 is used for removing tenacious soft tissue overlying the facet joint. The rasp 50 has a body 52 with a bore extending coaxially therethrough. The body 52 has an outer perimeter sized to fit within the working port 36. A shaft 54 extends through the bore and has a roughened surface 56 on a distal end 58. The shaft 54 includes an actuating feature 60 on a proximal end that is used for actuating or rotating the roughened surface 56. In the exemplary embodiment, the actuated end may be adapted to couple with a hand held or powered device, such as an electric motor for example, that rotates the shaft 54 and the roughened surface 56. In the exemplary embodiment, the rasp 50 is made from a bio-compatible material such as but not limited to titanium, stainless steel, or radiolucent plastic such as PEEK. In one embodiment, the body 52 has a diameter of 5-18 millimeters and a length of about 30 millimeters.

A drill device 62 is shown in FIG. 4 for forming a circular hole into the patients facet joint. The drill includes a cylindrical body 64 having a stop feature 66 on a proximal end. The stop feature 66 contacts the proximal end of the working sleeve 32 to prevent the drill device 62 from entering the spinal canal. The body 64 has an outer perimeter sized to fit and rotate within the working port 36. The body 64 includes a center bore that receives a shaft 68. A drill member 70 is coupled to the distal end of the shaft 68. The drill member 70 has a conical tip that is smooth with the cutting features formed on the sides, sometimes referred to as a side-cutting drill. The drill member 70 has a length that is sized to be slightly longer than the height of the graft 74 (FIG. 7). The drill device 62 further includes an actuating feature 72 that allows either manual actuation or coupling with a powered device, such as an electric motor for example. In the exemplary embodiment, the drill device 62 is made from a bio-compatible materials such as but not limited to titanium, stainless steel, or radiolucent plastic such as PEEK. It should be appreciated that the alignment of the drill device 62 with the pedicle screw guide wire provides advantages in locating the drill member 70 at the desired facet joint surface to allow decorticating of the joint and proper preparation for fusion of the facet joint. In one embodiment, the body 64 has a diameter of 15-18 millimeters and a length of about 30 millimeters. In one embodiment, the drill member 70 has a diameter of about 5-18 millimeters. In another embodiment, the drill member 70 has a diameter of about 5-10 millimeters.

Figure 6:
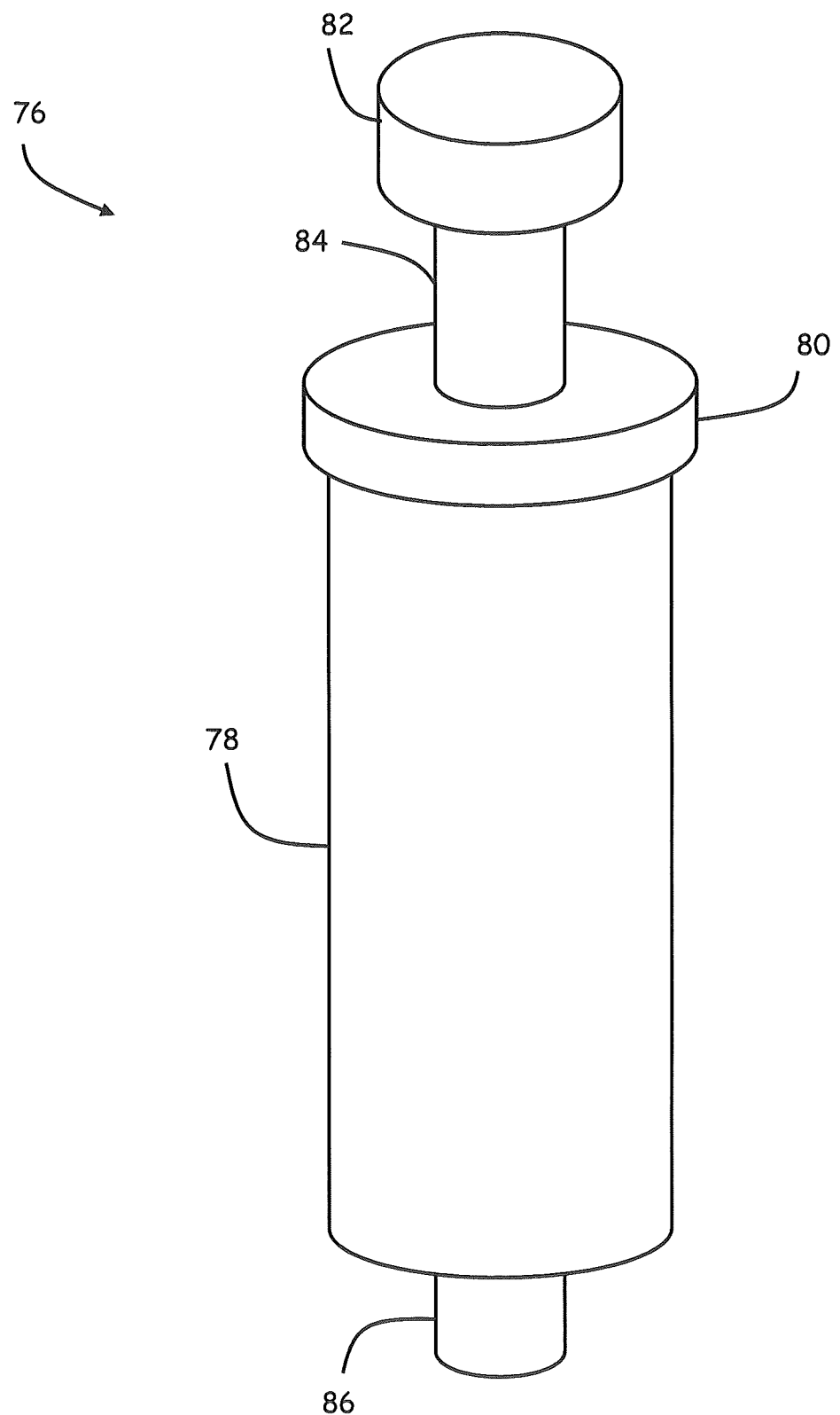
FIG. 6 is a perspective view of a graft material insertion device for use with the working sleeve of FIG. 2; and, FIG. 7A-7J are views of graft devices with use with the insertion device of FIG. 6.

A graft insertion device 76 is shown in FIG. 6 for assisting the surgeon in the placement of the graft 74 in the hole formed by the drill device 62. The graft insertion device 76 includes a cylindrical body 78 has an outer perimeter that is sized to fit within the working port 36. The body 78 includes a stop feature 80 that contacts the proximal end of the working sleeve 32 to allow malleting or rotation of the body 78 or the tamp 82. The body 78 may include a cylindrical or rectangular bore that is sized to receive the shaft 84 of tamp 82. The shaft 84 includes a distal end 86 that includes a feature for coupling with the graft 74. In one embodiment, the body 78 has a diameter of about 15-18 millimeters and a length of about 30 millimeters.

Figure 7A:
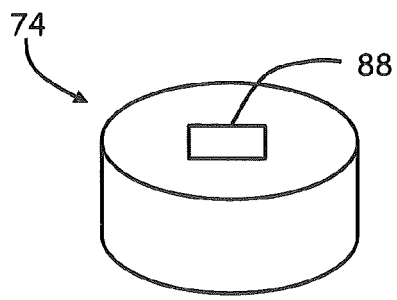
Figure 7B:
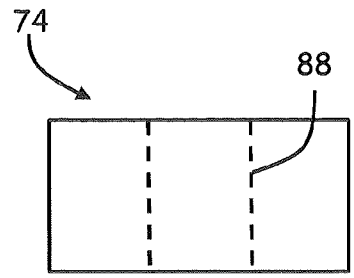
Figure 7C:
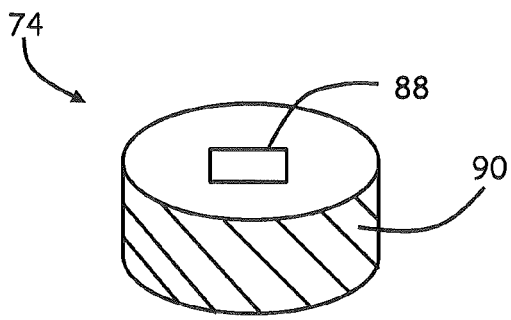
Figure 7D:
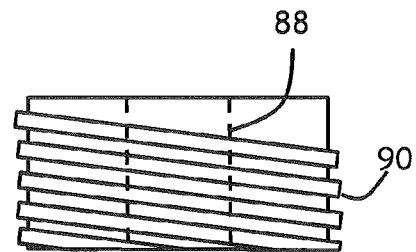
Figure 7E:
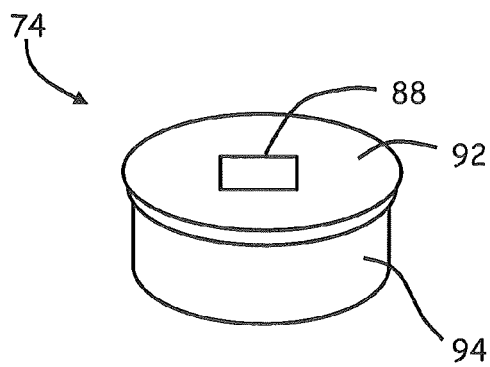
Figure 7F:
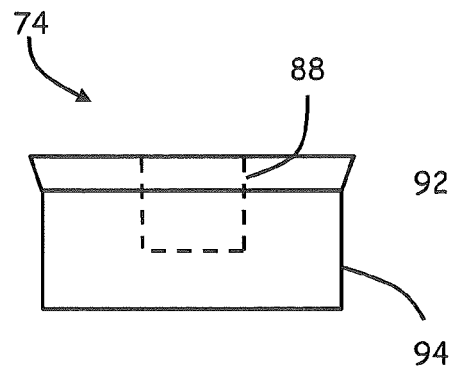

FIGS. 7A and 7B show a first embodiment of a circular graft 74 that is sized to fit within the hole formed by the drill member 70. In the exemplary embodiment, the graft 74 has an outer diameter of about 5-18 millimeters. In one embodiment, the graft 74 has an outer diameter of about 5-10 millimeters. In another embodiment, the graft 74 has an outer diameter that is slightly larger than the drill member 70. The graft 74 includes a feature 88 that couples with the end 86 of tamp 82 to allow insertion via the working port 36. A second embodiment is shown in FIGS. 7C and 7D shows a circular graft 74 having an external thread 90 disposed about the outer surface of the graft 74. FIGS. 7E and 7F show a third embodiment of the circular graft 74 made from two different materials. In this embodiment, the graft 74 includes a cortical bone portion 92 on one end and a cancellous bone portion 94 on an opposite end. The beveled surface 96 of the cancellous portion 94 provides advantages in resistance to backing out of the graft.

Figure 7G:
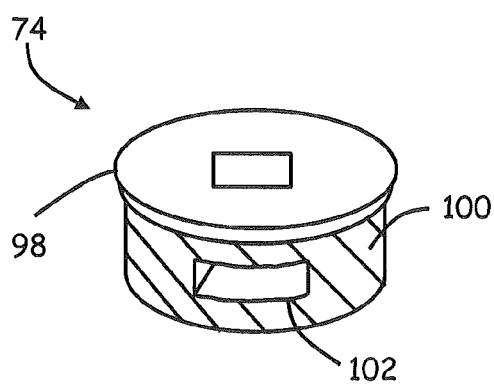
Figure 7H:
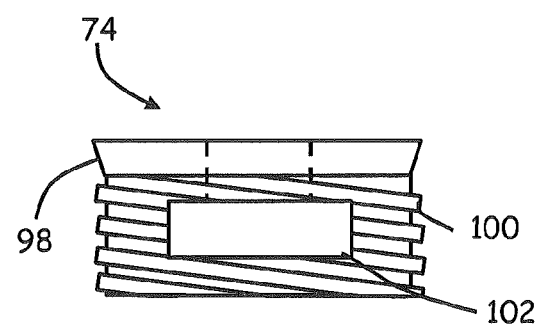
Figure 7I:
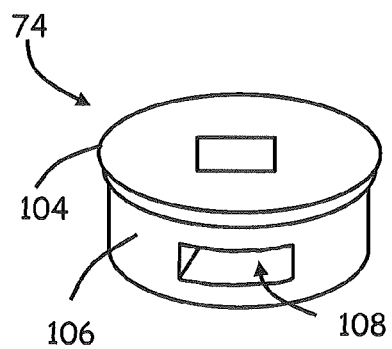
Figure 7J:
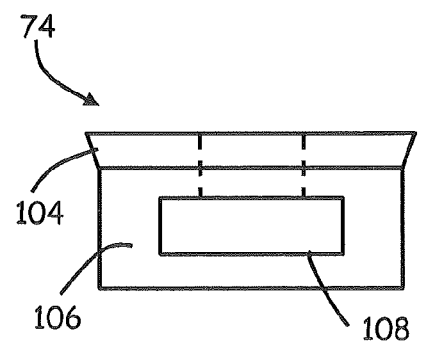

FIGS. 7G and 7H show a fourth embodiment of the circular graft 74 having a beveled cortical top 98 with a threaded body portion 100. An opening 102 is provided in the threaded body portion 100 to accept other materials including bone graft substitute materials, such as demineralize bone matrix for example, or bioactive molecules such as a hormone for example. A fifth embodiment is shown in FIGS. 7I and 7J of a circular graft 74 having a beveled cortical top 104 and a smooth body 106. An opening 108 is provided in the body 106 transverse to the longitudinal axis. The opening 108 is disposed to accept other materials.

During a procedure, the surgeon first makes an incision sized for a minimally invasive spinal fusion procedure. The guide wire is placed on the pedicle using standard radiographic assisted techniques. The guide wire sleeve 20 is placed over the guide wire such that the guide wire is within the channel 28. The portion 26 is arranged to prevent the guide wire sleeve 20 from entering the spinal canal. With the guide wire sleeve 20 in place, the surgeon slides the guide wire and guide wire sleeve 20 into the port 38 of working sleeve 32. The working sleeve 32 is slid into position with the teeth 42 engaging the patient's bone.

With the working sleeve 32 engaging and secured within the incision, the surgeon may insert the soft tissue dissector 43 into the port 36. By sliding the dissector 43 longitudinally within the port 36, the end 48 may be used to displace tissue that blocks access to the area of interest. Once a sufficient amount of tissue is displaced, the surgeon removes the dissector 43 and inserts the rasp 50. The rasp 50 is malleted onto the bone and the roughed surface 56 is moved using the actuating feature 60 to remove soft tissue that is overlying the facet joint.

Once a sufficient amount of soft tissue is removed, the rasp 50 is removed from the working sleeve 32 and the drill 62 is inserted until contacting the facet joint. The actuating feature 72 is rotated, either manually or with the assistance of a powered device, to form a round hole in the facet joint. With the hole formed, the surgeon removes the drill 62 and couples a circular graft 74 onto the end 86 of the insertion tool 76. The insertion tool 76 is slid through the port 36 to engage the graft 74 with the hole formed by the drill 62. Depending on the type of graft 74 being used, the graft 74 may be either screwed into or malleted into the hole using the tamp 82. With the graft 74 in place, the surgeon may then remove the working sleeve 32 and guide wire sleeve 20. With these devices removed, the surgeon performs other steps to complete the surgery without interfering with the graft 74 insertion.

It should be appreciated that while embodiments herein refer to the implementing devices having bodies with a diameter, this is for exemplary purposes and the claimed invention should not be so limited. In one embodiment, the ports 36, 38 may have perimeters configured to accept other shaped implementing device, such as a square or elliptical cross section for example.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

The invention claimed is:

1. A spinal facet fusion device comprising:
a working sleeve having a first surface with a first port and a second port extending therethrough parallel to a longitudinal axis, the working sleeve having a length and a width, wherein the length is larger than the width, the first port having a first perimeter and the second port having a second perimeter, wherein the first port is larger than the second port, the working sleeve having a feature on a distal surface configured to engage a facet joint bone;
a guide wire sleeve having a body with a proximal end and a distal end and a first outer perimeter, the first outer perimeter being sized and shaped to be axially slidingly disposed within the second port, the guide wire sleeve having a channel extending longitudinally from the proximal end through the distal end, the body further having a stop feature on the distal end, the stop feature being larger than the second perimeter; and,
an implementing device having a second outer perimeter sized to be slidingly received within the first perimeter.

2. The device of claim 1 wherein the implementing device is selected from a group consisting of a soft tissue dissector, a rasp, a drill and an insertion device.

3. The device of claim 2 wherein the distal surface is arranged to removably contact the stop feature.

4. The device of claim 2 wherein the implementing device is a drill, the drill having a member shaped to form a round hole.

5. The device of claim 4 further comprising a round graft device sized to be received within the round hole.

6. The device of claim 5 wherein the graft device has a thread disposed on an outer diameter.

7. The device of claim 5 wherein the graft device includes a cortical bone portion and a cancellous bone portion.

8. The device of claim 5 wherein the graft device includes an opening extending transverse to an axis of the graft device.

9. The device of claim 1 wherein the guide wire sleeve body includes marking indicia on the proximal end, the marking indicia being configured to provide an indication to a surgeon of the relative position of the implementing device.

10. The device of claim 9 wherein the stop feature has a spherical shape.

11. A spinal facet fusion device comprising:
a working sleeve having a first surface and a second surface, the working sleeve having an oval cross sectional shape, the working sleeve having a first port and a second port extending through the first surface and the second surface parallel to a longitudinal axis of the working sleeve, the first port having a first perimeter and the second port having a second perimeter, wherein the first port is larger than the second port, the second surface having features for engaging a patient's facet joint bone;
a guide wire sleeve having a first body with a proximal end and a distal end and a first outer perimeter, the first outer perimeter being sized and shaped to be axially slidingly disposed within the second port, the guide wire sleeve having a channel extending longitudinally from the proximal end through the distal end, the first body further having a first stop feature on the distal end, the stop feature being larger than the second port, wherein the second surface is removably in contact with the first stop feature; and, an implementing device having a second outer perimeter sized to be slidingly received within the first perimeter.

12. The device of claim 11 wherein the implementing device is selected from a group consisting of a soft tissue dissector, a rasp, a drill and an insertion device.

13. The device of claim 12 wherein the implementing device is a soft tissue dissector, the soft tissue dissector having an attachment feature on one end, the attachment feature having a third outer perimeter, the third outer perimeter being larger than the first perimeter.

14. The device of claim 12 wherein the implementing device is a rasp, the rasp having a roughened surface on one end and an actuating feature on an opposite end.

15. The device of claim 12 wherein the implementing device is a drill, the drill having a second body having a shaft rotatingly coupled thereto, the shaft having a side cutting drill on one end and an actuating feature on an opposite end, the second body having a second stop feature on an end adjacent the actuating feature, the second stop feature having a fourth outer perimeter, the fourth outer perimeter being larger than the first perimeter.

16. The device of claim 15 wherein the side cutting drill is shaped to form a round hole.

17. The device of claim 16 further comprising a graft device, the graft device having an outer diameter sized to couple with the round hole.

18. A spinal facet fusion device comprising:
a working sleeve having an oval shaped first body, the first body having a length that is dimensionally larger than a width, the body having a first surface and a second surface arranged on opposing ends, the first body having an asymmetrically arranged first port and a second port extending longitudinally therethrough, the first port having a first perimeter and the second port having a second perimeter, wherein the first port is larger than the second port, the second surface having features for engaging a patient's facet joint bone;
a guide wire sleeve having a second body with a proximal end and a distal end and a first outer perimeter, the first outer perimeter being sized and shaped to be removably disposed within and axially slidable relative to the second port, the guide wire sleeve having a channel extending longitudinally from the proximal end through the distal end, the second body further having a rounded stop feature on the distal end, the stop feature being larger than the second port, wherein the second surface is configured to be in removable contact with the stop feature; and,
an implementing device having a second outer perimeter sized to be received within the first perimeter, the implementing device being longitudinally movable within the first port.

19. The device of claim 18 wherein the guide wire sleeve body includes marking indicia on the proximal end, the marking indicia being configured to provide an indication to a surgeon of the relative position of the implementing device when the implementing device is positioned within the first port.

* * * * *